(12) United States Patent
Morishita et al.

(10) Patent No.: US 8,067,388 B2
(45) Date of Patent: Nov. 29, 2011

(54) DECOY-CONTAINING PHARMACEUTICAL COMPOSITIONS AND METHOD OF USING THE SAME

(75) Inventors: Ryuichi Morishita, Osaka (JP); Motokuni Aoki, Osaka (JP); Toshio Ogihara, Osaka (JP); Tomio Kawasaki, Osaka (JP)

(73) Assignee: AnGes MG, Inc., Osaka (JP)

( * ) Notice: Subject to any disclaimer, the term of this patent is extended or adjusted under 35 U.S.C. 154(b) by 317 days.

(21) Appl. No.: 12/349,824

(22) Filed: Jan. 7, 2009

(65) Prior Publication Data

US 2010/0331395 A1 Dec. 30, 2010

Related U.S. Application Data

(63) Continuation of application No. 11/580,748, filed on Oct. 12, 2006, now Pat. No. 7,524,830, which is a continuation of application No. 10/466,239, filed as application No. PCT/JP02/00865 on Feb. 1, 2002, now abandoned.

(51) Int. Cl.
- *A61K 31/70* (2006.01)
- *C07H 21/02* (2006.01)
- *C07H 21/04* (2006.01)
- *C12Q 1/68* (2006.01)

(52) U.S. Cl. ............... 514/44 R; 514/44 A; 436/23.1; 436/24.1; 436/24.5; 435/375

(58) Field of Classification Search ............. None
See application file for complete search history.

(56) References Cited

U.S. PATENT DOCUMENTS

| | | | |
|---|---|---|---|
| 5,225,212 A | 7/1993 | Martin et al. | |
| 5,575,815 A | 11/1996 | Slepian et al. | |
| 6,262,033 B1 | 7/2001 | Morishita et al. | |
| 6,271,206 B1 | 8/2001 | Pillai et al. | |
| 6,303,582 B1 | 10/2001 | Eljamal | |
| 6,559,168 B2 | 5/2003 | Marfat et al. | |
| 6,821,956 B2 * | 11/2004 | Dzau et al. | 514/44 R |
| 7,034,007 B1 | 4/2006 | Nyce et al. | |

FOREIGN PATENT DOCUMENTS

| | | |
|---|---|---|
| EP | 0 824 918 A1 | 2/1998 |
| EP | 1 008 352 A1 | 6/2000 |
| EP | 1 170 363 A1 | 1/2002 |
| JP | 2002-193813 | 7/2002 |
| WO | WO 96/35430 A1 | 11/1996 |
| WO | WO 01/57204 A1 | 8/2001 |
| WO | WO 01/83713 | 11/2001 |

OTHER PUBLICATIONS

Laitinen et al Pharmacological Research vol. 37(4):251-254, 1998.*
Abe et al., "Specific inhibition of influenza virus RNA polymerase and nucleoprotein gene expression by circular dumbbell RNA/DNA chimeric oligonucleotides containing antisense phosphodiester oligonucleotides," *FEBS Letters*, 425(1):91-96 (1998).
Ardaillou et al., "Production et activite proinflammatoire de necrose tumorale alpha dans le glomerule," *L'Acadernie Nationale de Medecine*, 179:103-116 (1995).
Attiga et al., "Inhibitors of prostaglandin synthesis inhibit human prostate tumor cell invasiveness and reduce the release of matrix metalloproteinases," *Cancer Research*, 60:4629-4637 (2000).
Baker et al., "Matrix metalloproteinases, their tissue inhibitors and colorectal cancer staging," *British Journal of Surgery*, 87: 1215-1221 (2000).
Bene et al., "Subcellular Localization as a Limiting Factor for Utilization of Decoy Oligonucleotides," *Nucleic Acids Research*, 32(19), e142, (2004).
Bond et al., "Nuclear factor κB activity is essential for matrix metalloproteinase-1 and -3 upregulation in rabbit dermal fibroblasts," *Biochemical and Biophysical Research Communications*, 264:561-567 (1999).
Bond et al., "Synergistic upregulation of metalloproteinase-9 by growth factors and inflammatory cytokines: an absolute requirement for transcription factor NF-κB," *FEBS Letter*, 435:29-34 (1998).
Brunner et al., "Single bilayer vesicles prepared without sonication physico-chemical properties," *Biochimica et Biophysica Acta Biomembranes*, 455(2):322-331 (1976).
Chabaud et al., "Contribution of interleukin 17 to synovium matrix destruction in rheumatoid arthritis," *Cytokine*, 12(7):1092-1099 (2000).
Chu et al., "The Stability of Different Forms of Double-Stranded Decoy DNA in Serum and Nuclear Extracts," *Nucleic Acids Research*, 20:5857-5858, (1992).
Deamer, "Preparation and properties of ether-injection liposomes," *Annals of the New York Academy of Sciences*, 308:250-258 (1978).
Denhardt, "Oncogene-initiated aberrant signaling engenders the metastatic phenotype: synergistic transcription factor interactions are targets for cancer therapy," *Critical Reviews in Oncogenesis*, 7(3 &4):261-269 (1996).
Eberhardt et al., "Amplification of IL-1β-induced matrix metalloproteinase-9 expression by superoxide in rat glomerular mesangial cells is mediated by increased activities of NF-κB and activating protein-1 and involves activation of the mitogen-activated protein kinase pathways," *Journal of Immunology*, 165:5788-5797 (2000).
Farias et al., "Plasma metalloproteinase activity is enhanced in the euglobulin fraction of breast and lung cancer patients," *International Journal of Cancer*, 89:389-394 (2000).
Gaetani et al., "Metalloproteases and intracranial vascular lesions," *Neurological Research*, 21:385-390 (1999).

(Continued)

*Primary Examiner* — Sean McGarry
(74) *Attorney, Agent, or Firm* — Ropes & Gray LLP; James F. Haley, Jr.

(57) ABSTRACT

A pharmaceutical composition is provided for treatment and prevention of a disease caused by expression of a gene controlled by NF-κB or ets. The composition comprises at least one decoy and a pharmaceutically acceptable carrier. The decoy is an NF-κB decoy, an ets decoy, or a chimera decoy of NF-κB and ets. The disease is cerebral aneurysm, cancer, Marfan's syndrome, aortic detachment, post-angioplasty restenosis, chronic articular rheumatism, asthma, atopic dermatitis, nephritis, renal failure, or plaque rupture. The pharmaceutically acceptable carrier may be a hydrophilic polymer.

6 Claims, 10 Drawing Sheets
(5 of 10 Drawing Sheet(s) Filed in Color)

OTHER PUBLICATIONS

Gambarotta et al., "*Ets* up-regulates *MET* transcription," *Oncogene*, 13:1911-1917 (1996).

Griesenbach et al., "Cytoplasmic Deposition of NFκB Decoy Oligonucleotides is Insufficient to Inhibit Bleomycin-induced Pulmonary Inflammation," *Gene Therapy*, 9:1109-1115, (2002).

Halloran et al., "Pathogenesis of Aneurysms," *Seminars in Vascular Surgery*, 8(2):85-92 (1995).

Hayashi et al., "Enhanced expression of membrane type-1 matrix metalloproteinase in mesangial proliferative glomerulonephritis," *Journal of the American Society of Nephrology*, 9:2262-2271 (1998).

Hernandez-Presa et al., "ACE Inhibitor Quinapril Reduces the Arterial Expression of NF-κB-Dependent Proinflammatory Factors but not of Collagen I in a Rabbit Model of Atherosclerosis", *American Journal of Pathology*, 153:1825-1837 (1998).

Holmes et al., "Indomethacin prevents elastase-induced abdominal aortic aneurysms in the rat," *Journal of Surgical Research*, 63:305-309 (1996).

Horikawa et al., "Association of latent membrane protein 1 and matrix metalloproteinase 9 with metastasis in nasopharyngeal carcinoma," *Cancer*, 89:715-723 (2000).

Ikeda et al , "Inhibition of gelatinolytic activity in tumor tissues by synthetic matrix metalloproteinase inhibitor: application of film in situ zymography," *Clinical Cancer Research*, 6:3290-3296 (2000).

Jeffery, P.K., "Differences and Similarities Between Chronic Obstructive Pulmonary Disease and Asthma," *Clinical and Experimental Allergy*, 29(Suppl. 2):14-26, (1999).

Jia et al., "Suppression of human microvascular endothelial cell invasion and morphogenesis with synthetic matrixin inhibitors," *Angiogenesis: From the Molecular to Integrative Pharmacology*, Edited by Maragoudakis, Kluwer Academic/Plenum Publishers, New York (2000).

Jiang, et al., "Invasiveness of Hepatocellular Carcinoma Cell Lines: Contribution of Hepatocyte Growth Factor, c-met, and Transcription Factor Ets-1," *Biochemical and Biophysical Research Communications*, 286, pp. 1123-1130 (2001).

Kaneda et al., "The role of the activated form of matrix metalloproteinase-2 in urothelial cancer," *BJU International*, 86:553-557 (2000).

Katz et al., "Abdominal Aortic Aneurysms," *Seminars in Vascular Surgery*, 8(4):289-298 (1995).

Khaled et al., "Use of Phosphorothioate-Modified Oligodeoxynucleotides to Inhibit NF-κB Expression and Lymphocyte Function," *Clinical Immunology and Immunopathology*, 86(2): 170-179, (1998).

Kim et al., "Lipopolysaccharide activates matrix metalloproteinase-2 in endothelial cells through an NF-κB-dependent pathway," *Biochemical and Biophysical Research Communications*, 269:401-405 (2000).

Kmiec, Eric B., "Gene Therapy," *American Scientist*, 87:240-243, 245-247, (1999).

Kraan et al., "Modulation of inflammation and metalloproteinase expression in synovial tissue by leflunomide and methotrexate in patients with active rheumatoid arthritis," *Arthritis & Rheumatism*, 43(8):1820-1830 (2000).

Kuper et al., "β-amyloid binds to p75$^{NTR}$ and activates NFκB in human nueroblastoma cells," *Journal of Neuroscience Research*, 54:798-804 (1998).

Lebruska et al., "Selection and Characterization of an RNA Decoy for Transcription Factor NF-κB," *Biochemistry*, 38:3168-3174, (1999).

Lee et al., *FASEB Journal*, 15:A663, #523.9, (2001).

Leff, Alan R., "Future Directions in Asthma Therapy," *Chest*, 111:61S-68S, (1997).

Lin et al., "Cancer chemoprevention by tea polyphenols through mitotic signal transduction blockade," *Biochemical Pharmacology*, 58:911-915 (1999).

Marti, "New strategy to treat glomerular inflammation by inhibition of mesangial cell matrix metalloproteinases," *Schweiz Med Wochenschr.*, 130(21):784-788 (2000).

Miyake et al., Inhibitory effect of chimera decoy oligodeoxynucleotides (ODN) against Ets and NFκB on progression of rabbit experimental aortic aneurysms (AAA), *Circulation*, 106(19):II-116 (2002).

Moore et al., "Suppression of experimental abdominal aortic aneurysms by systemic treatment with a hydroxamate-based matrix metalloproteinase inhibitor (RS 132908)," *Journal of Vascular Surgery*, 29:522-532 (1999).

Oda et al., "ETS-1 Converts Endothelial cells to the angiogenic phenotype by inducing the expression of matrix metalloproteinases and integrin $β_3$," *Journal of Cellular Physiology*, 1789:121-132 (1999).

Oikawa et al., "Hypoxia induces transcription factor ETS-1 via the activity of hypoxia-inducible factor-1," *Biochemical and Biophysical Research Communications*, 289:39-43 (2001).

Ono et al., "Decoy Administration of NF-κB into the Subarachnoid Space for Cerebral Angiopathy," *Human Gene Therapy*, 9:1003-1011 (1998).

Origuchi et al., "IL-1-mediated expression of membrane type matrix-metalloproteinase in rheumatoid osteoblasts," *Clinical and Experimental Rheumatology*, 18:333-339 (2000).

Pellegrini et al., "Simultaneous measurement of soluble carcinoembryonic antigen and the tissue inhibitor of metalloproteinase TIMP1 serum levels for use as markers of pre-invasive to invasive colorectal cancer," *Cancer Immunology Immunotherapy*, 49:388-394 (2000).

Peters et al., "Functional polymorphism in the matrix metalloproteinase-9 promoter as a potential risk factor for intracranial aneurysm," *Stroke*, 30:2612-2616 (1999).

Rayet et al., "Aberrant *rel/nfkb* genes and activity in human cancer," *Oncogene*, 18:6938-6947 (1999).

Royds et al., "Response of tumour cells to hypoxia: Role of p53 and NFκB," *Journal of Clinical Pathology: Molecular Pathology*, 51:55-61 (1998).

Sakata et al., "Expression of matrix metalloproteinases (MMP-2, MMP-9, MT1-MMP) and their inhibitors (TIMP-1, TIMP-2) in common epithelial tumors of the ovary," *International Journal of Oncology*, 17:673-681 (2000).

Sato et al., "Signal transduction and transcriptional regulation of angiogenisis," *Angiogenesis: From the Molecular to Integrative Pharmacology*, Maragoudakis, Kluwer Academic ed., pp. 109-115, Plenum Publishers (2000).

Segura et al , "Immunohistochemistry of matrix metalloproteinases and their inhibitors in thoracic aortic aneurysms and aortic valves of patients with Marfan's Syndrome," *Circulation*, 98:II-331-II-338 (1998).

Shin et al., "Effects of tumor necrosis factor-α and interferon-γ on expression of matrix metalloproteinase-2 and -9 in human bladder cancer cells," *Cancer Letters*, 159:127-134 (2000).

Sinha, et al., "Matrix Metalloproteinases and Abdominal Aortic Aneurysms: A Potential Therapeutic Target," *J. Clin. Pharmacol.*, 38, pp. 1077-1088 (1998).

Szoka et al., "Preparation of unilamellar liposomes of intermediate size (0.1-0.2 μm) by a combination of reverse phase evaporation and extrusion through polycarbonate membranes," *Biochimica et Biophysica Acta Biomembranes*, 601(3):559-571 (1980).

Tomita et al., "Transcription factor decoy for NFκB inhibits TNF-α-induced cytokine and adhesion molecule expression in vivo," *Gene Therapy*, 7:1326-1332 (2000).

Tomita, et al., "Transcription Factor Decoy for NκFB Inhibits Cytokine and Adhesion Molecule Expressions in Synovial Cells Derived From Rheumatoid Arthritis," *Rheumatology*, 39, pp. 749-757 (2000).

Treharne et al., "Marimastat inhibits elastin degradation and matrix metalloproteinase 2 activity in a model of aneurysm disease," *British Journal of Surgery*, 86:1053-1058 (1999).

Turner et al., "Role of matrix metalloproteinase 9 in pituitary tumor behavior," *Journal of Clinical Endocrinology & Metabolism*, 85(8):2931-2935 (2000).

Yamamoto et al., "Role of the NF-κB Pathway in the Pathogenesis of Human Disease States," *Current Molecular Medicine*, 1:287-296, (2001).

Yamanaka et al., "Expression and tissue localization of membrane-types 1, 2, and 3 matrix metalloproteinases in rheumatoid synovium," 80(5):677-687 (2000).

Yokoseki et al., "*cis* Element Decoy Against Nuclear Factor-κB Attenuates Development of Experimental Autoimmune Myocarditis in Rats," *Circulation Research*, 89(10):899-906 (2001).

Yoshihara et al., "Matrix metalloproteinases and tissue inhibitors of metalloproteinases in synovial fluids from patients with rheumatoid arthritis or osteoarthritis," *Annual Rheumatoid Diseases*, 59:455-461 (2000).

Yoshimura et al., "Inhibition of Intimal Hyperplasia After Balloon Injury in Rat Carotid Artery Model Using cis-Element 'Decoy' of Nuclear Factor-κB Binding Site as a Novel Molecular Strategy," *Gene Therapy*, 8:1635-1642 (2001).

Kaneda et al., "Hemagglutinating virus of Japan (HVJ) envelope vector as a versatile gene delivery system" Molecular Therapy, 6(2):219-226 (2002).

Altschul et al., "Basic local alignment search tool," *Journal of Molecular Biology*, 215(3):403-410 (1990).

Anderson, "Solution hybridization: RNA:DNA hybridization," *Nucleic Acid Hybridization*, Springer Bios Scientific Publishers, 4:1:35-47 (1999).

Gish et al., "Identification of protein coding regions by database similarity search," *Nature Genetics*, 3(3):266-272 (1993).

Hern-Ku et al., "Inhibition of murine asthmatic reactions by antisense oligonucleotide to p65 subunit of nuclear factor (NF)-κB," *FASEB Journal*, 15(4): A663 (2001).

Higgins et al., "Using CLUSTAL for multiple sequence alignments," *Methods in Enzymology*, 266:383-402 (1996).

Lung Disease Focus (http://www.lungdiseasefocus.com/articles/about-asthma/asthma-causes.php, last visited Jan. 25, 2008).

Pearson et al., "Improved tools for biological sequence comparison," *Proc Natl Acad Sci U S A.*, 85(8):2444-2448 (1988).

Thompson et al., "CLUSTAL W: improving the sensitivity of progressive multiple sequence alignment through sequence weighting, position-specific gap penalties and weight matrix choice," *Nucleic Acids Research*, 22(22):4673-4680 (1994).

Kaneda et al, "Gene therapy using HVJ-liposomes: the best of both worlds?," Molecular Medicine Today, 5:298-303 (1999).

Donnelly et al., " Therapy for chronic obstructive pulmonary disease in the 21st century," *Drugs*, 63(19):1973-1998 (2003).

Fujihara et al., "Inhibition of nuclear factor-kappaB activation unmasks the ability of TNF-alpha to induce human eosinophil apoptosis," *European Journal of Immunology*, 32(2):457-466 (2002).

Griesenbach et al., "Anti-inflammatory gene therapy directed at the airway epithelium," *Gene Therapy*, 7(4):306-313 (2000).

Wright et al., " The role of nuclear factor kappa B in the pathogenesis of pulmonary diseases: implications for therapy," *American Journal of Respiratory Medicine*, 2(3):211-219 (2003).

Zhang et al., "The therapeutic efficacy of nuclear factor kappaB decoy cis element in animal model of asthma," *Database BIOSIS* [Online] (PREV200400029562) pp. 1-2 (Oct. 2003) (abstract attached); *Zhonghua Weishengwuxue He Mianyixue Zazhi*, 23(10):753-758 (2003).

Sequence Search Result in 2008 for SEQ ID No. 1 against SEQ ID No. 2655 of Nyce et al., U.S. Patent 7,034,007.

UniProt, www.uniprot.org/taxOnomy/11198, as retrieved on Oct. 23, 2008.

\* cited by examiner

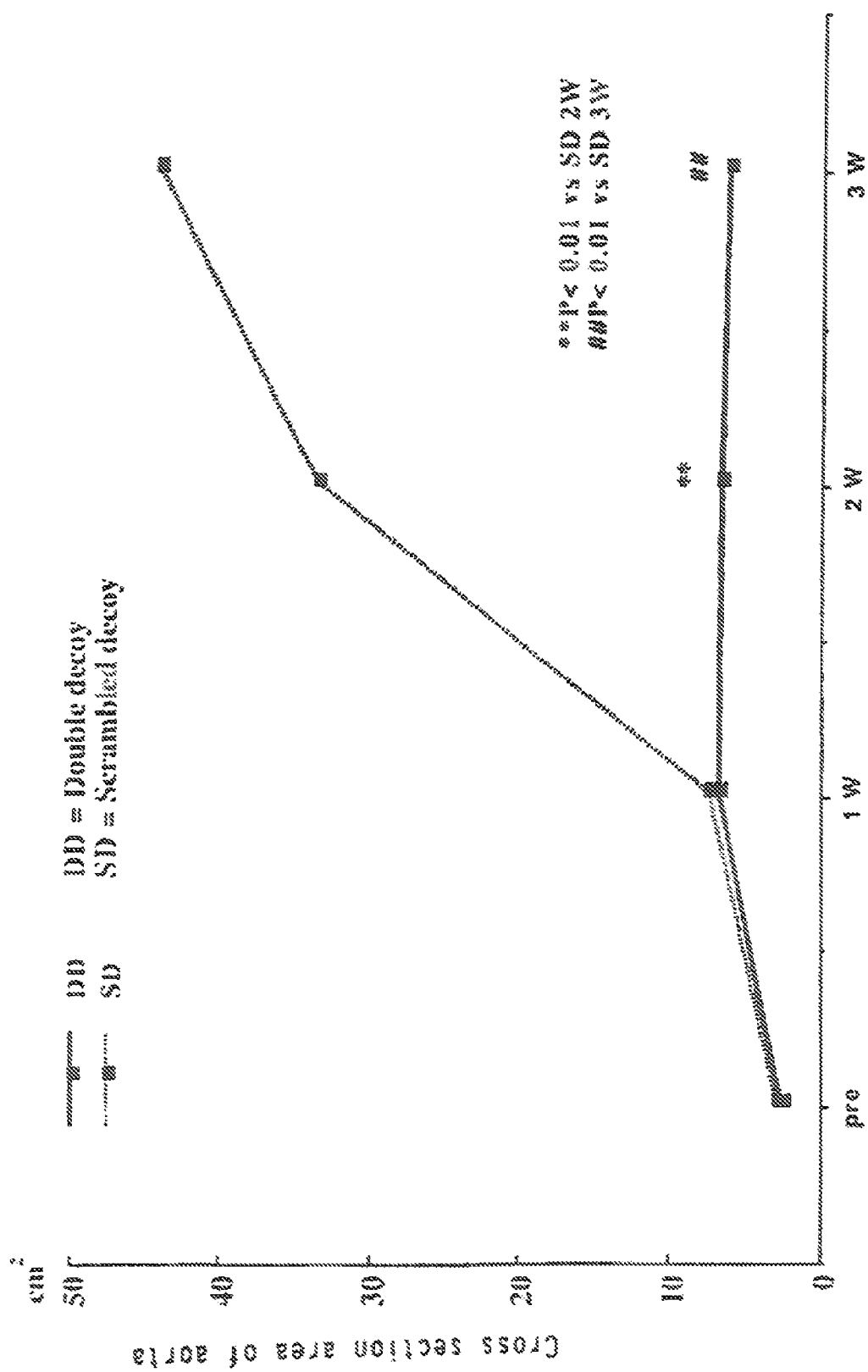

DECOY-CONTAINING PHARMACEUTICAL COMPOSITIONS AND METHOD OF USING THE SAME

CROSS REFERENCE TO RELATED APPLICATION

This application is a continuation of U.S. patent application Ser. No. 11/580,748, filed Oct. 12, 2006 now U.S. Pat. No. 7,524,830, which is a continuation of U.S. patent application Ser. No. 10/466,239, filed Jul. 10, 2003 now abandoned, which was a 371 application of PCT/JP02/00865, filed Feb. 1, 2002, which designates the United States.

TECHNICAL FIELD

The present invention relates to a composition comprising a compound (e.g., a nucleic acid and a homolog thereof) which specifically binds to a site on a chromosome, to which site a transcriptional regulatory factor binds, and a method of using the same. More particularly, the present invention relates to a composition comprising a decoy compound and a method of using the same.

BACKGROUND ART

A variety of diseases including asthma, cancers, heart diseases, aneurysms, autoimmune diseases, and viral infections manifest varying symptoms and signs and yet it has been suggested that an abnormal expression (an overexpression or underexpression) of one or a few proteins is a major etiologic factor in many cases. In general, the expression of those proteins is controlled by a variety of transcriptional regulatory factors such as transcription activating factors and transcription suppressing genes.

NF-κB is a transcriptional regulatory factor consisting of heterodimers p65 and p50. NF-κB is typically localized in the cytoplasm where NF-κB is bound by its inhibitory factor Iκ so that intranuclear movement of NF-κB is prevented. However, when a stimulus, such as cytokine, ischemia, reperfusion, or the like, is applied due to any cause, IκB is degraded by phosphorylation. As a result, NF-κB is activated and transferred into the nucleus. In the nucleus, NF-κB binds to an NF-κB binding site on a chromosome and promotes the transcription of a gene downstream thereof. As genes located downstream of the NF-κB binding site, for example, inflammatory cytokines (e.g., IL-1, IL-6, IL-8, tumor necrosis factor α (INF α), etc.) and adhesion molecules (e.g., (e.g., VCAM-1, ICAM-1, etc.) are known.

NF-κB may be involved in the onset of progression of tumor malignancy (Rayet B et al., Oncogene 1999 Nov. 22; 18(49)6938-47); NF-κB is involved in response of tumor cells to hypoxia stress (Royds J A et al., Mol Pathol 1998 April; 51(2):55-61); NF-κB inhibits expression of cytokines and adhesion molecules in synovial membrane cells derived from chronic rheumatoid arthritis patients (Tomita T et al., Rheumatology (Oxford) 2000 July; 39(7):749-57); suppression of coordination between a plurality of transcriptional factors including NF-κB changes the malignant phenotypes of various tumors (Denhardt D. T., Crit. Rev. Oncog., 1996; 7(3-4):261-91); downregulation of NF-κB activation due to green tea polyphenol blocks induction of nitric oxide synthesizing enzyme, and suppresses A431 human epidermoid carcinoma cells (Lin J. K., et al., Biochem. Pharmacol., 1999, Sep. 15; 58(6):911-5); amyloid β peptide observed in the brains of Alzheimer's disease patients binds to 75-kD neurotrophic receptor (p75$^{NTR}$) in neuroblastoma cells to activate NF-κB in a time-dependent manner and a dose-dependent manner (Kuper P, et al., J. Neurosci. Res., 1998, Dec. 15; 54(6):798-804); TNF-α, which is activated by NF-κB, plays an important role in the onset of glomerulonephritis (Ardaillou et al., Bull. Acad. Natl. Med., 1995, Jan; 179(1)103-15); NF-κB decoy in vivo blocks expression of cytokines and adhesion molecules in mouse nephritis induced by TNF α (Tomita N., et al., Gene Ther., 2000, Aug.; 7(15)1326-32); and the like.

It was suggested that NF-κB suppresses MMP1 and MMP9, members of matrix metalloproteinase (MMP), at the transcription level (Eberhardt W., Huwiler A., Beck K. F., Walpen S., Pfeilschifter J., "Amplification of IL-1β-induced matrix metalloproteinase-9 expression by superoxide in rat glomerular mesangial cells is mediated by increased activities of NF-κB and activating protein-1 and involves activation of the mitogen-activated protein kinase pathways", J. Immunol., 2000, Nov. 15, 165(10), 5788-97; Bond M., Baker A. H., Newby A. C., "Nuclear factor KB activity is essential for matrix metalloproteinase-1 and -3 upregulation in rabbit dermal fibroblasts", Biochem. Biophys. Res. Commun., 1999, Oct. 22, 264 (2), 561-7; Bond M., Fabunmi R. P., Baker A. H., Newby A. C., "Synergistic upregulation of metalloproteinase-9 by growth factors and inflammatory cytokines: an absolute requirement for transcriptional factor NF-κB", FEBS Lett., 1998, Sep. 11, 435(1), 29-34; and Kim H., Koh G., "Lipopolysaccharide activates matrix metalloproteinase-2 in endothelial cells through an NF-κB-dependent pathway", Biochem. Biophys. Res. Commun., 2000, Mar. 16, 269(2), 401-5).

MMP is a polygene family of zinc-dependent enzymes involved in degradation of extracellular matrix components. It is also known that ets suppresses MMP1 and MMP9, members of matrix metalloproteinase (MMP), at the transcription level (Sato Y., Abe M., Tanaka K., Iwasaka C., Oda N., Kanno S., Oikawa M., Nakano T., Igarashi T., "Signal transduction and transcriptional regulation of angiogenesis", Adv. Exp. Med. Biol., 2000, 476, 109-15; and Oda N., Abe M., Sato Y., "ETS-1 converts endothelial cells to the angiogenic phenotype by inducing the expression of matrix metalloproteinases and integrin β3", J. Cell Physiol., 1999, February, 178 (2), 121-32).

MMP plays an important role in invasion of cancer cells by mediating degradation of extracellular matrix protein. A number of studies suggested the involvement of MMP and MMP inhibitors (TIMP) in the progression of cancer: the TIMP1 level in serum may be used as a marker for prognosis and diagnosis of colon and rectum cancer, and as a selective marker for metastatic cancer (Pellegrinl P., et al., Cancer Immunol. Immunother., 2000 September; 49 (7):388-94); expression and activity of MMP2 and MMP9 in human urinary bladder cancer cells are affected by tumor necrosis factor α and γ interferon (Shin K Y et al., Cancer Lett 2000 Oct. 31; 159 (2):127-134); MMP2, MMP9 and MT1-MMP, and their inhibitors, TIMP1 and TIMP2, are expressed in ovarian epithelium tumor (Sakata K., et al., Int. J. Oncol., 2000, Oct.; 17 (4):673-681); the level of each of MMP1, MMP2, MMP3 and MMP9 and the overall MMP activity are upregulated in colon and rectum tumor, and MMP1 is most important for progression of colon and rectum cancer (Baker E. A., et al., Br. J. Surg., 2000, September; 87(9):1215-1221); activated MMP2 plays an important role in invasion of urothelial cancer, and also the expression level of the activated MMP2 can be used as a useful prognosis index (Kaneda K., et al., BJU Int., 2000, September; 86(4):553-557); a prostaglandin synthesis inhibitor inhibits invasion of human prostate tumor cells, and reduces the release of MMP (Attiga F. A., et al., Cancer Res., 2000, Aug. 15; 60(16):4629-37); the MMP activity of a serum euglobulin fraction increases in breast cancer and lung cancer patients, and may be used as a tumor marker for these cancers (Farias E., et al., Int. J. Cancer, 2000, Jul. 20; 89(4):389-94); a MMP inhibitor inhibits gelatin-degrading activity in tumor cells (Ikeda M., et al., Clin. Cancer Res., 2000, Aug.; 6(8):3290-6); induction of MMP9 due to a membrane protein LMP1 contributes to metastatic of nasopharyngeal cancer (NPC) (Horikawa T., et al., Cancer, 2000, Aug. 15; 89(4):715-23); MMP plays an important role in an early stage of angioplasty, and a MMP inhibitor suppresses invasion and morphogenesis of human microvascular endothelial cells (Jia M. C., et al., Adv. Exp. Med. Biol., 2000; 476:181-94); MMP9 is expressed in invasive and recurrent pituitary adenoma and hypophysis cancer (Turner H. E., et al., J. Clin. Endocrinol. Metab., 2000, August; 85(8):2931-5); and the like.

MMP is also known to be involved in development of aortic aneurysm: MMP is involved in formation and rupture of cerebral aneurysm (Gaetani P., et al., Neurol. Res., 1999, Jun.; 21(4):385-90); a MMP-9 promotor is a risk factor for cerebral aneurysm (Peters D. G., et al., Stroke, 1999, December; 30(12):2612-6); inhibition of MMP inhibits the growth of microaneurysm in an aneurysm model (Treharne G. D., et al., Br. J. Surg., 1999, August; 86(8):1053-8); and the like.

MMP is secreted from migrating vascular smooth muscle cells, macrophage, and the like, and destroys collagen, elastin, and the like present in blood vessel walls, whereby the tension of the blood vessel is lost and the blood vessel does not resist the blood pressure and its diameter is expanded. In fact, in the blood vessel of an aneurysm, significant destruction of elastin is observed (Halloran B. G., Baxter B. T., "Pathogenesis of aneurysms", Semin. Vasc. Surg., 1995, Jun. 8, (2):85-92).

Aortic aneurysmal rupture is substantially fatal. To prevent aortic aneurysmal rupture, it is important to remove risk factors of arteriosclerosis. However, it is difficult to eliminate the risk factors. At present, invasive surgery is the only means for preventing aortic aneurysmal rupture.

According to data obtained by measuring the aorta diameter of from 35-year-old to 80-year old adult males, the average was 1.5 cm to 2.0 cm (Dolores J Katz, James C. Stanley, Gerald B. Zelenock, "Abdominal Aortic Aneurysms", Seminars in Vascular Surgery, vol. 8, No. 4 (December), 1995; pp. 289-298). In general, the aorta having a diameter beyond 1.5 times as great as the average value is judged as an aortic aneurysm. However, according to the above-described data, one in every 400 people had an aneurysm having a diameter of 3 cm or more which is judged as aortic aneurysm. Therefore, although the degree of risk of aorta rupture is not considered here, the prevalence of aortic aneurysm is relatively high in from 35-year-old to 80-year old adult males. The prevalence is believed to be even greater in males aged 65 and above.

It is known that MMPs are involved in chronic articular rheumatism: alleviation of chronic articular rheumatism by drug treatment leads to a decrease in MMP1 within synovial membrane tissue (Kraan M. C., et al., Arthritis Rheum., 2000, August; 43(8):1820-30); upregulation of MT-MMP expression by IL-1β partially induces activation of MMP-2, leading to cytokine-mediated articular disruption in chronic articular rheumatism (Origuchi T., Clin. Exp. Rheumatol., 2000, May-Jun.; 18(3):333-9); inflammatory cytokine IL-17 produced in synovial membrane of chronic articular rheumatism increases production of MMP1 (Chabaud M., et al., Cytokine, 2000, Jul.; 12(7):1092-9); MMP1, MMP2, MMP3, MMP8, MMP9 and an MMP inhibitor are present in the chronic articular rheumatism synovia at a high level, when MMPs are activated, the balance with the MMP inhibitor is lost, resulting in cartilage disruption (Yoshihara Y., et al., Ann. Rheum. Dis., 2000, June; 59(6):455-61); MT1-MMP is involved in activation of proMMP-2 in rheumatic synovial membrane lining cell layers, leading to cartilage disruption in chronic articular rheumatism (Yamanaka H., et al., Lab. Invest., 2000, May; 80(5):677-87); and the like.

MMP is involved in cardiovascular lesions due to Marfan's syndrome (Segura A. M., et al., Circulation, 1998, Nov. 10; 98(19 Suppl):11331-7).

Expression of membrane type MMP (MT-MMP) is increased in mesangial proliferative glomerulonephritis (Hayashi K., et al., J. Am. Soc. Nephroi., 1998, Dec.; 9(12):2262-71).

It has been reported that a MMP inhibitor suppresses the expansion of a blood vessel diameter in an aortic aneurysm model in rat abdomen (Moore G., Liao S., Curci J. A., Starcher B. C., Martin R. L., Hendricks R. T., Chen J. J., Thompson R. W., "Suppression of experimental abdominal aortic aneurysms by systemic treatment with a hydroxamate-based matrix metalloproteinase inhibitor" (RS 132908), J. Vasc. Surg., 1999, Mar.; 29(3):522-32).

A MMP inhibitor may be used in therapy for glomerulonephritis (Marti H P, Schweiz Med Wochenschr 2000 May 27; 130(21); 784-8). However, systemic administration of a MMP inhibitor causes severe side effects, and has difficulty in clinical applications for treatment (therapy and prevention) of various diseases.

It has been suggested that NF-κB is involved in various diseases via expression of a number of genes under the transcription control thereof. However, no method for effectively treating these diseases, particularly a non-invasive treatment method, has been provided. Particularly, as described above, aortic aneurysm is not a rare disease. As society ages, an increase in arteriosclerotic diseases inevitably leads to an increase in aortic aneurysm diseases. Considering the aging of patients, it is ideal to suppress directly the growth of aortic aneurysm using a pharmaceutical agent, however, to date such a means is not present. There is a desperate demand for development of a low-invasive therapy and prevention method for aortic aneurysm.

DISCLOSURE OF THE INVENTION

The present invention provides a composition suitable for treatment of the above-described various diseases caused by expression of a gene controlled by NF-κB or ets, and a method of using the same.

The present invention provides a composition comprising a NF-κB decoy, an ets decoy, or a chimera (double) decoy of NF-κB and ets as a major ingredient, which is used to treat and/or prevent various diseases caused by expression of a gene controlled NF-κB or ets, and a method for treating the diseases.

The present inventors found that administration of a NF-κB or ets decoy or a chimera (double) decoy of NF-κB and ets is effective for treatment of diseases caused by expression of a gene controlled by NF-κB or ets. Thus, the present invention was completed.

The present invention relates to a pharmaceutical composition for treatment and prevention of a disease caused by expression of a gene controlled by NF-κB or ets. The composition comprises at least one decoy and a pharmaceutically acceptable carrier.

The decoy is preferably an NF-κB decoy or an ets decoy, and more preferably a chimera (double) decoy of NF-κB and ets.

Preferably, the disease is cerebral aneurysm, cancer, Marfan's syndrome, aortic detachment, post-angioplasty restenosis, chronic articular rheumatism, asthma, atopic dermatitis, nephritis, renal failure, or plaque rupture.

Preferably, the pharmaceutically acceptable carrier is a hydrophilic polymer.

BRIEF DESCRIPTION OF THE DRAWINGS

This application file contains at least one drawing executed in color. Copies of this patent or patent application publication with color drawings will be provided by the United States Patent and Trademark Office upon request and payment of the necessary fee.

FIG. 10 shows the result of a test using the pharmaceutical composition of the present invention.

BEST MODE FOR CARRYING OUT THE INVENTION

Figure 1:
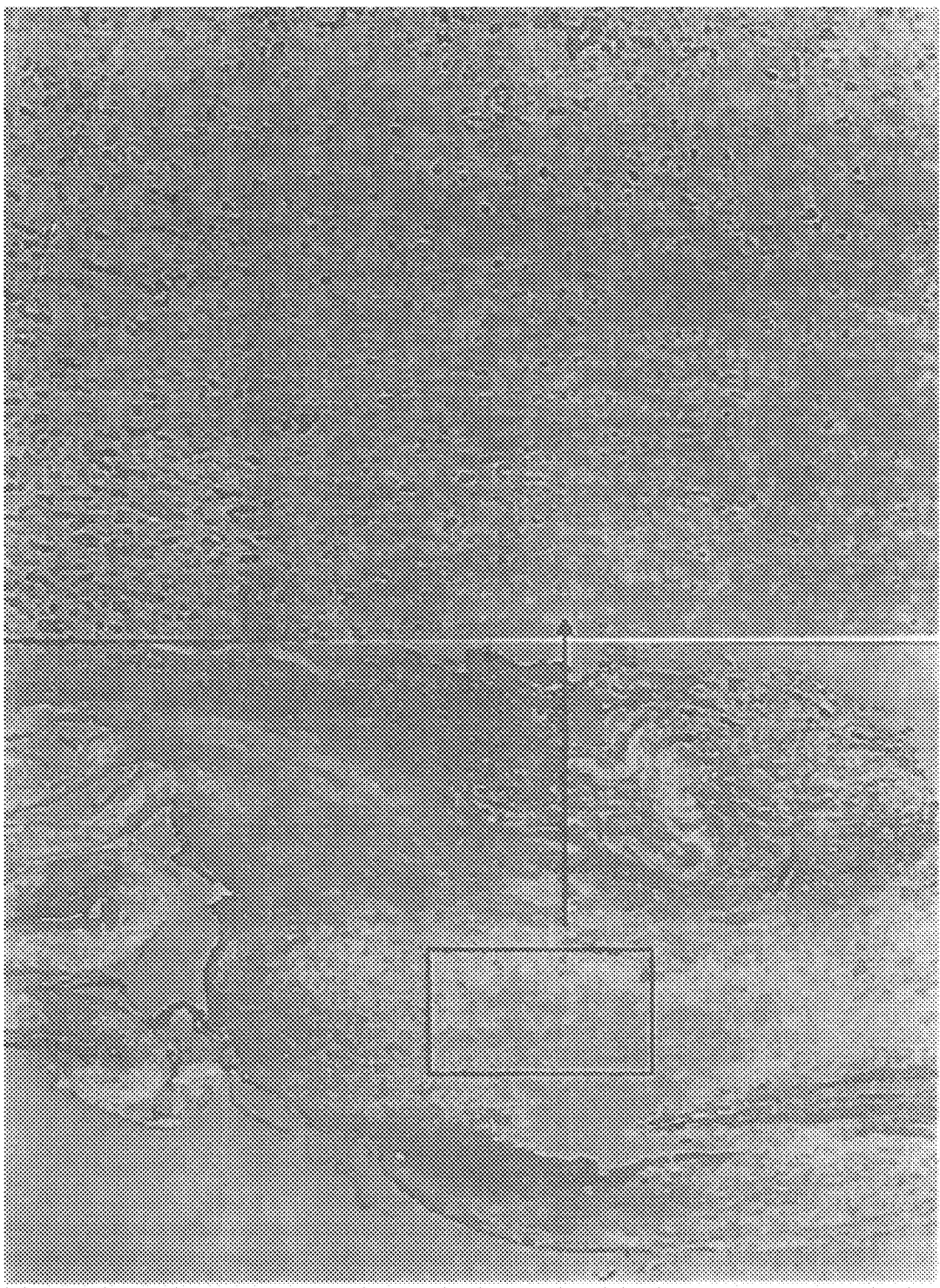
FIG. 1 shows light micrographs of the most expanded portions of the human aorta.

The term "decoy" or "decoy compound" refers to a compound which binds to a site on a chromosome, which NF-κB or ets binds to, or a site on a chromosome, which another transcription regulatory factor for a gene controlled by NF-κB or ets (hereinafter referred to as a target binding site) binds to, and antagonizes the binding of NF-κB, ets, or other transcriptional factors to these target binding sites. Representatively, the decoy or the decoy compound includes a nucleic acid and analogs thereof.

When a decoy is present within a nucleus, the decoy conflicts with a transcription regulatory factor competing for a target binding site for the transcription regulatory factor. As a result, a biological function which would be generated by binding of the transcription regulatory factor to the target binding site is inhibited. The decoy contains at least one nucleic acid sequence capable of binding to a target binding sequence. A decoy can be used for preparation of a pharmaceutical composition according to the present invention as long as the decoy can bind to a target binding sequence.

Preferable examples of a decoy include, but are not limited to, 5'-CCT-TGA-AGG-GAT-TTC-CCT-CC-3' (SEQ ID NO. 1) (NF-κB decoy); 5'-AAT-TCA-CCG-GAA-GTA-TTC-GA-3' (SEQ ID NO. 3) (ets decoy); 5'-ACC-GGA-AGT-ATG-AGG-GAT-TTC-CCT-CC-3' (SEQ ID NO. 5) (chimera (double) decoy of NF-κB and ets); an oligonucleotide containing a complement thereof; a variant thereof; and a compound including one or more of these molecules. The oligonucleotides may also include a modified nucleic acid and/or pseudonucleic acid therein. Further, these oligonucleotides may be mutants thereof, or compounds containing them therein. The oligonucleotides may have a single strand or double strands, or may be linear or annular. The mutants are nucleic acids having the above-described sequences, a part of which has a mutation, a substitution, an insertion, or a deletion, and which specifically antagonize NF-κB, or another transcription regulatory factor for a gene controlled by NF-κB, with respect to the nucleic acid binding site to which the factor binds. More preferable examples of the decoy for NF-κB and ets, or the other transcription regulatory factor for a gene controlled by NF-κB, include double-strand oligonucleotides containing one or a plurality of the above-described nucleic acid sequences, or mutants thereof. Nucleic acids containing one or a plurality of the above-described nucleic acid sequences are called chimera (double) decoy when the number of nucleic acid sequences contained is two, or triple decoy when the number of nucleic acid sequences contained is three, indicating the number of nucleic acid sequences.

The oligonucleotides for use in the present invention include oligonucleotides modified so as to resist in vivo degradation, and the like, such as oligonucleotides (S-oligo) having a thiophosphatediester bond which is a phosphatediester bond whose oxygen atom is replaced with a sulfur atom, oligonucleotides whose phosphatediester bond is substituted with a methylphosphate group having no electronic charge, and the like.

The decoy of the present invention can be produced with chemical or biochemical synthesis methods known in the art. For example, when a nucleic acid is used as a decoy compound, nucleic acid synthesis methods commonly used in genetic engineering can be employed. For example, a DNA synthesizer may be used to directly synthesize intended decoy nucleic acids. Further, these nucleic acids, nucleic acids containing the nucleic acids, or parts thereof may be synthesized, followed by amplification using a PCR method, a cloning vector, and the like. Furthermore, nucleic acids obtained by these methods are cleaved using a restriction enzyme, or the like, and linked or the like using DNA ligase, or the like to produce an intended nucleic acid. To obtain decoy nucleic acids which are more stable in cells, base, sugar and phosphate portions of the nucleic acids may be subjected to chemical modification, such as alkylation, acylation, or the like.

The present invention provides a pharmaceutical composition comprising the above-described decoy compound alone or in combination with a stabilizing compound, a diluent, a carrier or another component, or a pharmaceutical agent.

The pharmaceutical composition of the present invention may be used in such a form that the decoy is taken into cells in an affected part or cells in an intended tissue.

The pharmaceutical composition of the present invention is administered in any aseptic biocompatible pharmaceutical carrier (including, but not limited to, physiological saline, buffered physiological saline, dextrose, and water). A pharmaceutical composition of any of these molecules mixed with an appropriate excipient, an adjuvant, and/or a pharmaceutically acceptable carrier may be administered to patients alone or in combination with another pharmaceutical agent in a pharmaceutical composition. In an embodiment of the present invention, the pharmaceutically acceptable carrier is pharmaceutically inactive.

The administration of the pharmaceutical composition of the present invention is achieved orally or parenterally. Parenteral delivery methods include topical, intra-arterial (e.g., directly into tumor, aneurysm, etc.), intramuscular, subcutaneous, intramedullary, into subarachnoid space, intraventricular, intravenous, intraperitoneal, or intranasal administrations. In addition to a decoy compound, the pharmaceutical composition comprises a pharmaceutically acceptable carrier, such as an excipient and other compounds for accelerating the processing of the decoy compound so as to prepare a pharmaceutically acceptable formulation. The further details of techniques for prescription and administration are described in, for example, the latest version of "REMINGTON'S PHARMACEUTICAL SCIENCES" (Maack Publishing Co., Easton, Pa.).

A pharmaceutical composition for oral administration may be prepared using a pharmaceutically acceptable carrier well known in the art in an administration form suitable for administration. Such a carrier can be prepared as a tablet, a pill, a sugar-coated agent, a capsule, a liquid, a gel, a syrup, a slurry, a suspension, or the like, which is suited for the patient to take the pharmaceutical composition.

The pharmaceutical composition for oral use may be obtained in the following manner: an active compound is combined with a solid excipient, the resultant mixture is pulverized if necessary, an appropriate compound is further added if necessary to obtain a tablet or the core of a sugar-coated agent, and the granular mixture is processed. The appropriate excipient may be a carbohydrate or protein filler, including, but not being limited to, the following: sugar including lactose, sucrose, mannitol, or sorbitol; starch derived from maize, wheat, rice, potato, or other plants; cellulose such as methylcellulose, hydroxypropylmethylcellulose, or sodium carboxymethylcellulose; and gum including gum Arabic and gum tragacanth; and protein such as gelatin and collagen. A disintegrant or a solubilizing agent such as crosslinked polyvinyl pyrrolidone, agar, alginic acid or a salt thereof (e.g., sodium alginate) may be used if necessary.

The sugar-coated agent core is provided along with an appropriate coating, such as a condensed sugar solution. The sugar-coated agent core may also contain gum arabic, talc, polyvinyl pyrrolidone, carbopolygel, polyethylene glycol, and/or titanium dioxide, a lacquer solution, and an appropriate organic solvent or a solvent mixed solution. To identify a product, or characterize the amount of an active compound (i.e., dose), dye or pigment may be added to tablets or sugar-coated agents.

The pharmaceutical preparation which may be orally used may contain, for example, a soft sealed capsule consisting of a gelatin capsule, gelatin and coating (e.g., glycerol or sorbitol). The gelatin capsule may contain an active component mixed with a filler or binder such as lactose or starch, a lubricant such as talc or magnesium stearate, and optionally a stabilizer. In the soft capsule, the decoy compound may be dissolved or suspended in an appropriate liquid, such as fatty oil, liquid paraffin or liquid polyethylene glycol, with or without a stabilizer.

The pharmaceutical preparation for parenteral administration contains an aqueous solution of an active compound. For the purpose of injection, the pharmaceutical composition of the present invention is prepared in an aqueous solution, preferably Hank's solution, Ringer's solution, or a physiologically suitable buffer such as a buffered physiological saline. The aqueous suspension for injection may contain a substance for increasing the viscosity of a suspension (e.g., sodium carboxymethylcellulose, sorbitol, or dextran). Further, the suspension of the active compound may be prepared as an appropriate oily suspension. Appropriate lipophilic solvents or vehicles include fatty acid such as sesame oil, synthetic fatty acid ester such as ethyl oleate or triglyceride, or liposome. The suspension may contain a stabilizer which allows a high-concentration solution preparation, or an appropriate pharmaceutical agent or reagent for increasing the solubility of the compound, if necessary.

For topical or intranasal administration, an appropriate penetrant for the specific barrier to be penetrated may be used in the preparation. Such a penetrant is generally known in the art.

The pharmaceutical composition of the present invention may be produced using a method similar to method known in the art (e.g., conventional mixing, dissolution, rendering to granules, preparation of a sugar-coated agent, elutriation, emulsification, capsulation, inclusion, or freeze drying).

Preferably, in the case of parenteral administration, such as topical administration or infusion from a cervical portion to cell of an affected part or cells of an intended tissue, the pharmaceutical composition of the present invention may contain a synthetic or naturally-occurring hydrophilic polymer as a carrier. Examples of such a hydrophilic polymer include hydroxypropylcellulose and polyethylene glycol. The decoy compound of the present invention may be mixed with the above-described hydrophilic polymer in an appropriate solvent. The solvent may be removed by a method such as air drying. The resultant compound may be shaped into a desired form, such as sheet, and then may be given to a target site. Such a preparation containing a hydrophilic polymer has a small moisture content, and an excellent shelf life, and an excellent retentivity of the decoy compound since the preparation absorbs water to be turned into gel when used.

Such a sheet may include a hydrophilic sheet obtained by mixing polyhydric alcohol with a compound similar to the above-described composition components, such as cellulose or starch, or a derivative thereof, a synthetic polymer compound or the like and adjusting the hardness of the sheet.

Such a sheet may be placed in a target site under a laparoscope using a laparoscope technique, for example. Currently, laparoscopic surgery has been dramatically developed as a non-invasive technique. By combining the pharmaceutical composition of the present invention with the laparoscope technique, a method for treatment of diseases, which can be repeatedly used, may be provided.

Alternatively, when a nucleic acid or a modification thereof is employed as a decoy, the pharmaceutical composition of the present invention is advantageously used in a form which is generally used in gene introduction methods, such as a membrane fusion liposome preparation using Sendai virus (HVJ) or the like, a liposome preparation using endocytosis or the like, a preparation containing a cationic lipid such as Lipofectamine (Lifetech Oriental) or the like, or a viral preparation using a retrovirus vector, an adenovirus vector, or the like. Particularly, a membrane fusion liposome preparation is preferable.

The liposome preparation is any of the liposome constructs which are a large unilamellar vesicle (LUV), a multilammelar vesicle (MLV), and a small unilamellar vesicle (SUV). The LUV has a particle system ranging from about 200 to about 1000 nm. The MLV has a particle system ranging from about 400 to about 3500 nm. The SUV has a particle system ranging from about 20 to about 50 nm. The membrane fusion liposome preparation using Sendai virus or the like preferably employs MLV having a particle system ranging from 200 nm to 1000 nm.

There is no particular limitation on a method for producing liposomes as long as the liposomes hold a decoy. The liposomes can be produced by a commonly used method, such as, for example, a reversed phase evaporation method (Szoka, Fetal., Biochim. Biophys. Acta, Vol. 601 559 (1980)), an ether infusion method (Deamer, D. W.: Ann. N.Y. Acad. Sci., Vol. 308 250 (1978)), a surfactant method (Brunner, J et al.: Biochim. Biophys. Acta, Vol. 455 322 (1976)), or the like.

Examples of lipids for forming a structure of a liposome include phospholipids, cholesterols, nitrogen lipids, and the like. Generally, phospholipids are preferable, including naturally-occurring phospholipids, such as phosphatidylcholine, phosphatidylserine, phosphatidylglycerol, phosphatidylinositol, phosphatidylethanolamine, phosphatidic acid, cardiolipin, sphingomyelin, egg yolk lecithin, soybean lecithin, lysolecithin, and the like, or the corresponding phospholipids hydrogenated by a commonly used method, and in addition, synthetic phospholipids, such as dicetylphosphate, distearoylphosphatidylcholine, dipalmitoylphosphatidylcholine, dipalmitoylphosphatidylethanolamine, dipalmitoylphosphatidylserine, eleostearoylphosphatidylcholine, eleostearoylphosphatidylethanolamine, eleostearoylphosphatidylserine, and the like.

The lipids including these phospholipids can be used alone or with at least two in a combination. In this case, lipids having an atom group having a positive group, such as ethanolamine, choline, or the like, within the molecule can be used to increase the binding rate of an electrically negative decoy nucleic acid. In addition to the major phospholipids used to form liposomes, an additive, such as cholesterols, stearylamine, α-tocopherol, or the like, which are generally known as an additive for formation of liposomes, can be used.

The thus-obtained liposomes can additionally contain a substance for promoting membrane fusion, such as a membrane fusion promoting protein purified from Sendai virus, inactivated Sendai virus, Sendai virus, or the like, so as to accelerate uptake into cells at an affected site or cells in an intended tissue.

An exemplary method for producing a liposome preparation will be specifically described below. For example, the above-described substance for forming a liposome is dissolved along with cholesterol in an organic solvent, such as tetrahydrofuran, chloroform, ethanol, or the like. The resultant solution is put into an appropriate vessel, followed by removal of the solvent under reduced pressure, thereby forming a film of the liposome forming substance on an inside wall of the vessel. A buffer solution containing a decoy is added to the vessel followed by agitation. The above-described membrane fusion promoting substance is added to the resultant liposome if necessary, followed by isolation of the liposome. The thus-obtained liposome containing the decoy can be suspended in an appropriate solvent or can be freeze-dried and thereafter dispersed in an appropriate solvent. The resultant suspension can be used in treatment. The membrane fusion promoting substance may be added in the interim period after the isolation of the liposome and before use.

The pharmaceutical composition of the present invention includes a composition containing an effective amount of decoy compound which can achieve the intended purpose of the decoy compound. "Therapeutically effective amount" or "pharmacologically effective amount" are terms which are well recognized by those skilled in the art and which refer to an amount of pharmaceutical agent effective for production of an intended pharmacological effect. Therefore, the therapeutically effective amount is an amount sufficient for reducing the manifestation of the disease to be treated. A useful assay for confirming an effective amount (e.g., a therapeutically effective amount) for a predetermined application is to measure the degree of recovery from a target disease. An amount actually administered depends on an individual to be treated. The amount is preferably optimized so as to achieve a desired effect without a significant side effect. The determination of the therapeutically effective dose is within the ability of those skilled in the art.

A therapeutically effective dose of any compound can be initially estimated using either a cell culture assay or any appropriate animal model. The animal model is used to achieve a desired concentration range and an administration route. Thereafter, such information can be used to determine a dose and route useful for administration into humans.

The therapeutically effective amount refers to an amount of a decoy compound which results in amelioration of symptoms or conditions of a disease. The therapeutic effect and toxicity of such a compound may be determined by standard pharmaceutical procedures in cell cultures or experimental animals (e.g., $ED_{50}$, a dose therapeutically effective for 50% of a population; and $LD_{50}$, a dose lethal to 50% of a population). The dose ratio between therapeutic and toxic effects is a therapeutic index, and it can be expressed as the ratio of $ED_{50}/LD_{50}$. Pharmaceutical compositions which exhibit high therapeutic indices are preferable. The data obtained from cell culture assays and animal studies can be used in formulating a dosage range for use in humans. The dosage of such compounds lies preferably within a range of circulating concentrations that include the $ED_{50}$ with little or no toxicity. Such a dosage may vary within this range depending upon the dosage form employed, the susceptibility of a patient, and the route of administration. As an example, the dose of a decoy is appropriately selected depending on the age and other conditions of a patient, the type of a disease, the type of the decoy employed, and the like. For example, in the case of intravascular administration, intramuscular administration, and intraarticular administration, 1 μg to 100 mg can be generally administered once a day to several times a day.

The exact dose is chosen by an individual physician in view of the condition of a patient to be treated. Doses and administration are adjusted to provide a sufficient level of the active portion, or to hold a desired effect. Additional factors to be considered include the severity of the condition of a disease (e.g., the size and location of a tumor; the age, weight and sex of a patient; a diet-limiting time and frequency of administration, a combination of drugs, reaction susceptibility, and resistance/response to treatment). A sustained action pharmaceutical composition may be administered every 3 to 4 days, every week, or once per two weeks, depending on the half life and clearance rate of a specific preparation. Guidance for specific doses and delivery methods are provided in publications known in the art.

Medicaments containing the thus-obtained decoy as a major component can be administered in various manners, depending on the type of disease, the type of the decoy employed, and the like. For example, the medicament can be intravascularly administered, applied to the site of a disease, administered to the disease site, or intravascularly administered to the disease site, for ischemic diseases, inflammatory diseases, autoimmune diseases, and cancer metastasis and invasion, and cachexia. More specifically, for example, when PTCA is performed for infarct of an organ, the medicament can be administered into a blood vessel of an affected part at the same time or before or after the PTCA. In organ transplantation or the like, an organ to be transplanted may be treated in advance with a preparation for use in the present invention. Further, for example, the medicament can be infused directly to a joint in the case of chronic articular rheumatism or the like.

EXAMPLES

Hereinafter, the present invention will be described by way of examples. These examples are for illustrative purposes only. The present invention is not limited by these examples.

Example 1

Overexpression of ets-1 in Human Aortic Aneurysm Sample

Figure 2:
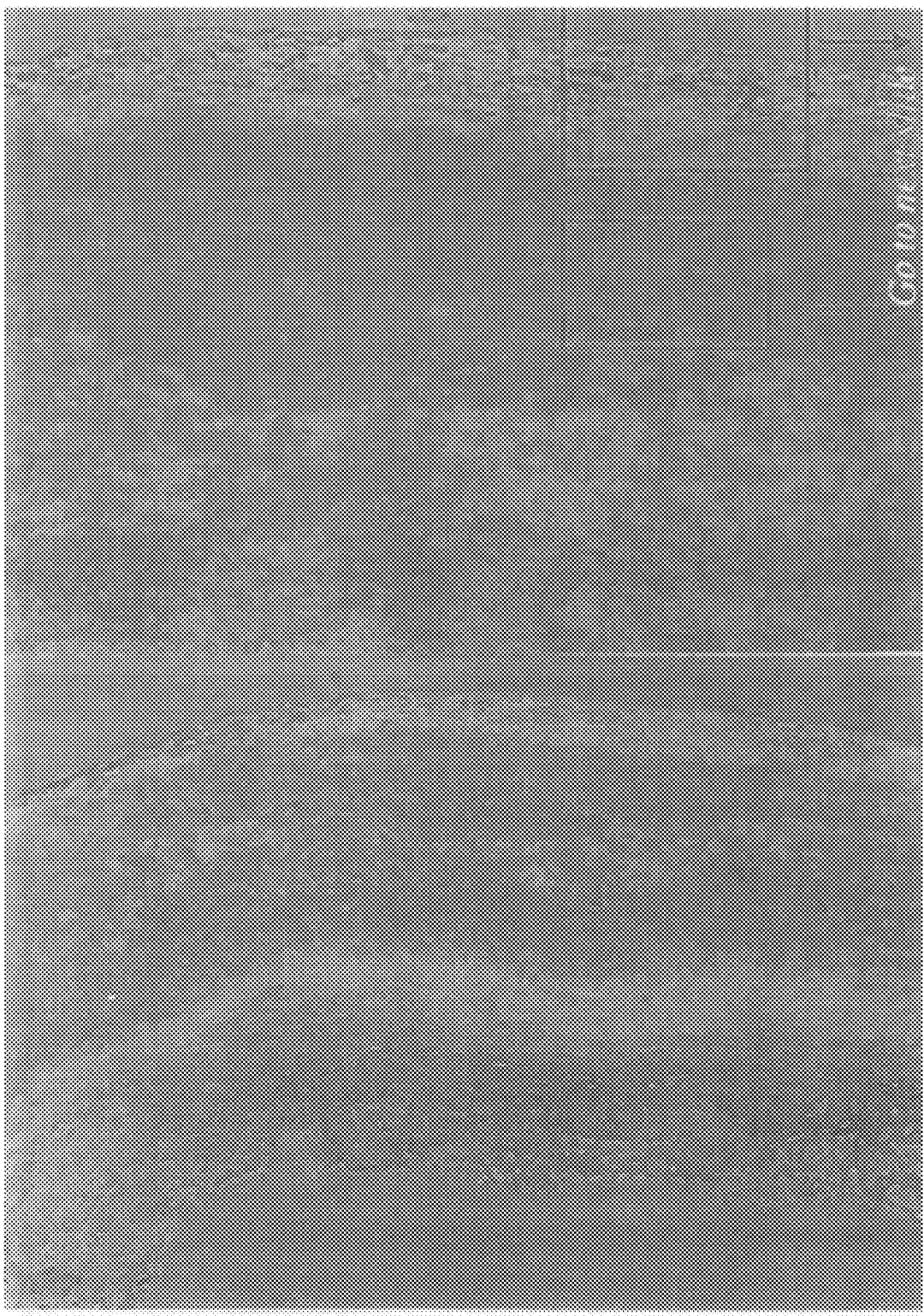
FIG. 2 shows light micrographs of the most expanded portions of the human aorta.
Figure 3:
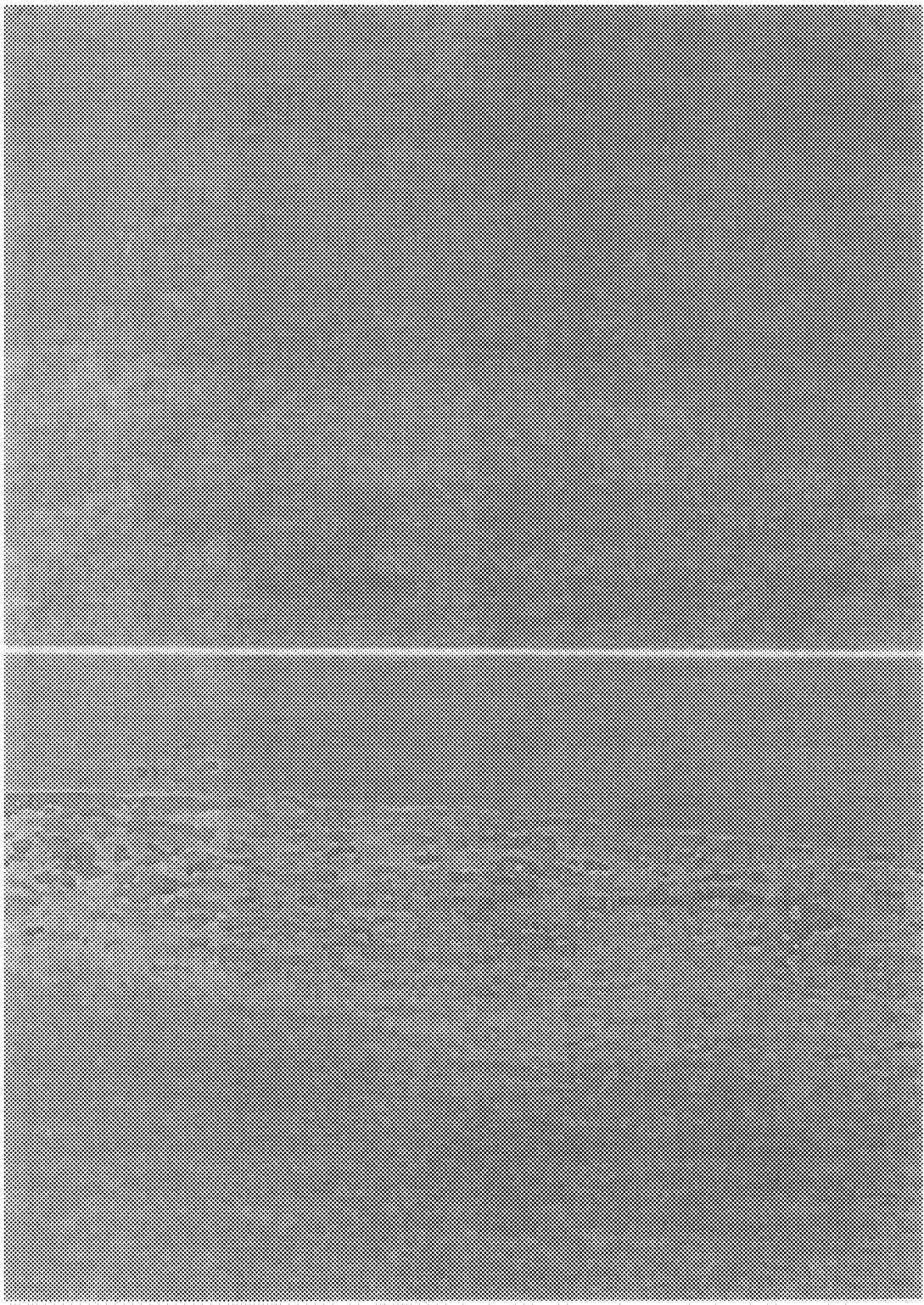
FIG. 3 shows light micrographs of the most expanded portions of the human aorta.

Ets-1 is one of the transcriptional factors which regulate expression of the MMP gene. Aortic aneurysm samples were surgically removed (excised) and fixed in formalin. The samples were subjected to commonly used immunostaining using an anti-ets-1 antibody (available from Santa Cruz Biotechnology (USA)). As shown in FIGS. 1, 2, and 3, the presence of ets-1 was confirmed in all of the aortic aneurysm samples, mainly the adventitia thereof.

A photograph to the left of FIG. 1 is a light micrograph showing the human aortic root (×100). A photograph to the right of FIG. 1 is an enlarged photograph (×400) of a rectangular section in the left photograph.

A photograph to the left of FIG. 2 is a light micrograph showing the human aortic root (×100).

A photograph to the left of FIG. 2 is a light micrograph (×100) of the most expanded portion of the human aorta. A photograph to the right of FIG. 2 is a fluorescent micrograph (×200) of the most expanded portion of the human aorta.

FIG. 3 are light micrographs (×400) of the most expanded portion of the human aorta, which are enlarged photographs of rectangular sections in FIG. 2. The photograph to the left of FIG. 3 is an enlarged photograph (×400) of the larger rectangular section in the right photograph of FIG. 3. The photograph to the left of FIG. 3 is an enlarged photograph (×400) of the smaller rectangular section in the right photograph of FIG. 3.

Example 2

Effect of Decoy Nucleic Acid in Organ Culture (Tissue Culture))

Aortic aneurysm samples surgically removed were used in organ culture (tissue culture) to test an effect of decoy nucleic acid transfer on suppression of MMP gene expression.

Human aortic aneurysm was surgically removed and divided into 2 mm$^2$ samples. The samples were immersed in 10% collagen gel containing 100 μM of a decoy or a scrambled decoy (synthesized by Hokkaido System Science) at room temperature for 1 hour. Thereafter, the samples were placed in 24-well plates with the gel being attached to the samples. 1.5 ml of culture medium (Dulbecco's modified Eagle's medium, 1% FCS) was added to each well, followed by culturing at 37° C. in an incubator. After 24 hours, the culture medium was removed and new culture medium was added to the plate. After another 48 hours, MMP1 and MMP9 in the culture medium were measured by a commonly used method using ELISA (manufactured by Amersham Pharmacia Biotech).

Decoys used herein:

```
NF-κB decoy                          (SEQ ID NO. 1)
5'-CCT-TGA-AGG-GAT-TTC-CCT-CC-3'
5'-GGA-GGG-AAA-TCC-CTT-CAA-GG-3'

NF-κB scrambled decoy                (SEQ ID NO. 2)
5'-TTG-CCG-TAC-CTG-ACT-TAG-CC-3'
5'-GGC-TAA-GTC-AGG-TAC-GGC-AA-3' ets decoy                            (SEQ ID NO. 3)
5'-AAT-TCA-CCG-GAA-GTA-TTC-GA-3'
5'-TCG-AAT-ACT-TCC-GGT-GAA-TT-3' ets scrambled decoy                  (SEQ ID NO. 4)
5'-GGA-ATA-CAT-CGA-CCT-GTT-AA-3'
5'-TTA-ACA-GGT-CGA-TGT-ATT-CC-3'
```

Figure 4:
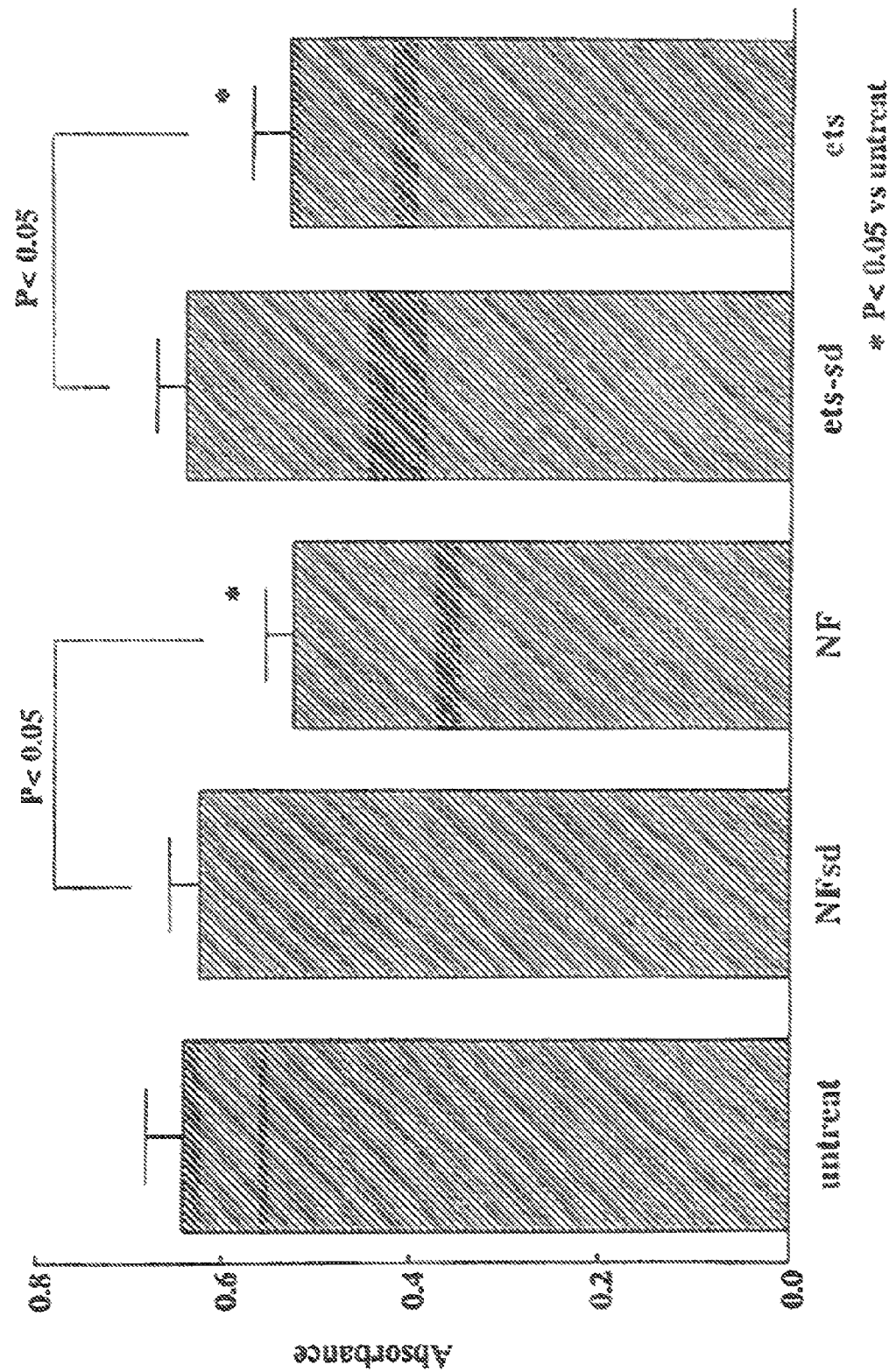
FIG. 4 shows the result of a test using the pharmaceutical composition of the present invention.
Figure 5:
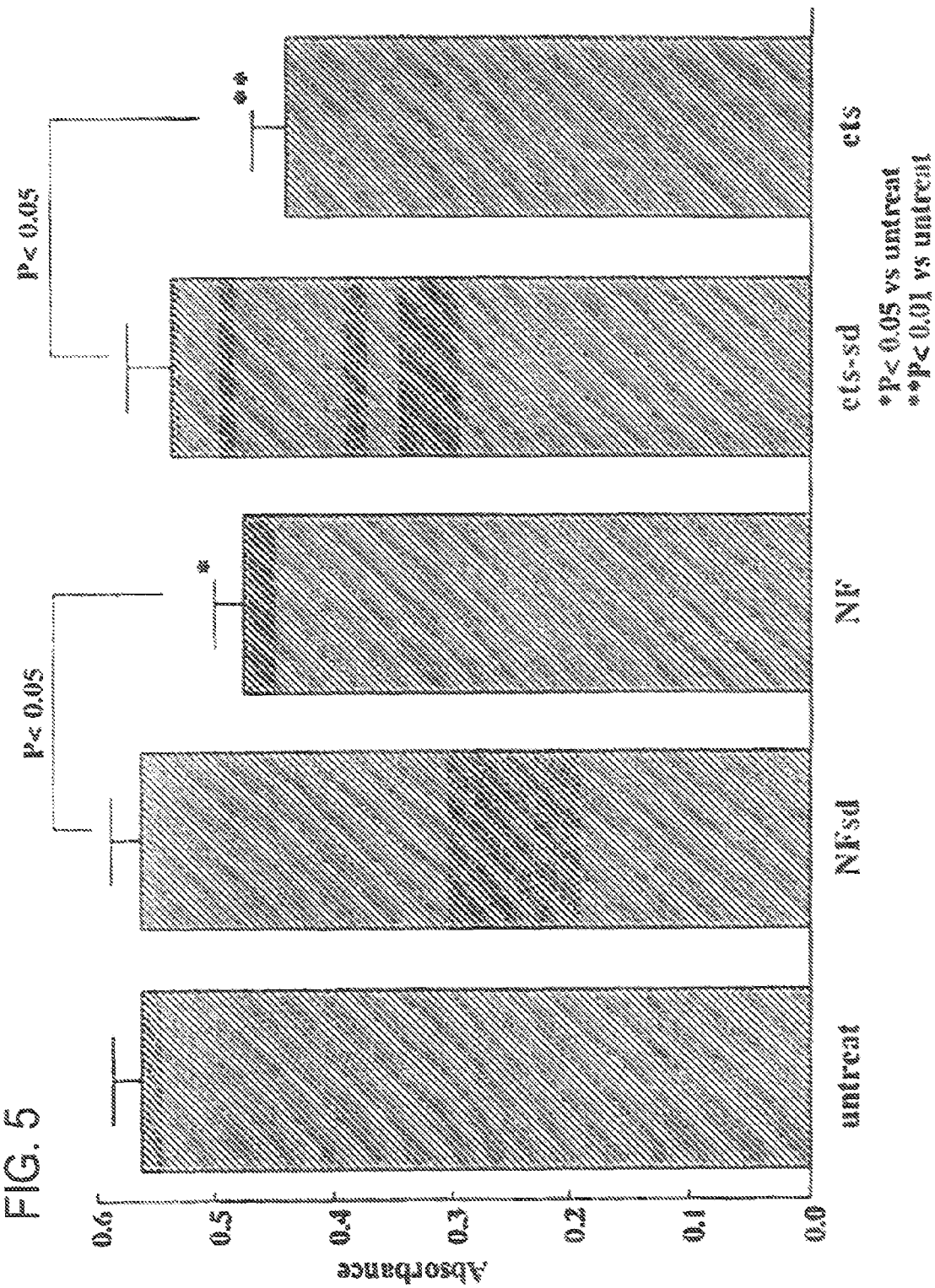
FIG. 5 shows the result of a test using the pharmaceutical composition of the present invention.

The results are shown in FIGS. 4 and 5. In FIGS. 4 and 5, the vertical axis represents absorbance at 450 nm, while "untreat", "NFsd", "NF", "ets-sd", and "ets" on the horizontal axis represent no nucleic acid reagent (control), NF-κB scrambled decoy, NF-κB decoy, ets scrambled decoy, and ets decoy, respectively. In FIGS. 4 and 5, a horizontal bar on each bar represents a standard deviation, and "P" on a line connected between each bar represents the level of significance which is used to compare groups connected via the line. "**" on a horizontal bar indicates that the average value of the corresponding group is different from the average of the control at a significance level of 1% (FIG. 4) or 5% (FIG. 5) (Fisher test).

As can be seen from FIGS. 4 and 5, in the ets decoy-administered group, production of MMP1 and MMP9 was significantly suppressed as compared to the control group and the ets scrambled decoy-administered group. Also, in the NF-κB decoy-administered group, production of MMP1 and MMP9 was significantly suppressed as compared to the control group and the NF-κB scrambled decoy-administered group.

Example 3

Concentration-Dependent Effect of Decoy Nucleic Acid and Double Decoy Nucleic Acid on Organ Culture (Tissue Culture System)

An effect of decoy nucleic acid addition on suppression of MMP gene expression was tested in organ culture (tissue culture system) by the same method as in Example 2, except that the added decoy nucleic acids were 100 μM and 600 μM NF-κB decoy, and 100 μM and 600 μM double decoy and double scrambled decoy having the following structure.

```
Double decoy                         (SEQ ID NO. 5)
5'-ACC-GGA-AGT-AGA-AGG-GAT-TTC-CCT-CC-3'
5'-GGA-GGG-AAA-TCC-CTT-CTA-CTT-CCG-GT-3'

Double scrambled decoy               (SEQ ID NO. 6)
5'-GCA-ACC-CCT-TAG-GTT-CTG-AGA-GAC-GA-3'
5'-GGA-GGG-AAA-TCC-CTT-CTA-CTT-CCG-GT-3'
```

Figure 6:
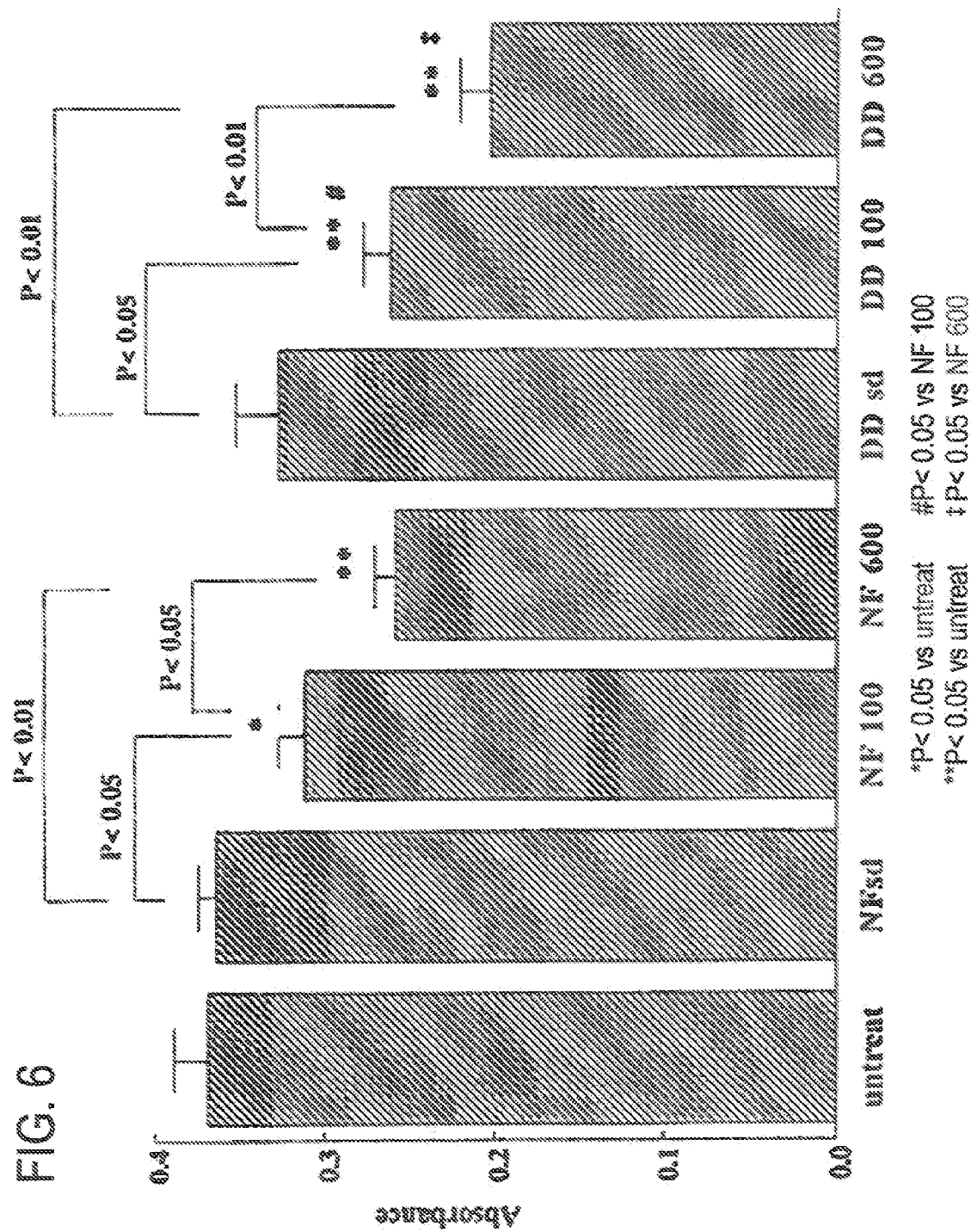
FIG. 6 shows the result of a test using the pharmaceutical composition of the present invention.
Figure 7:
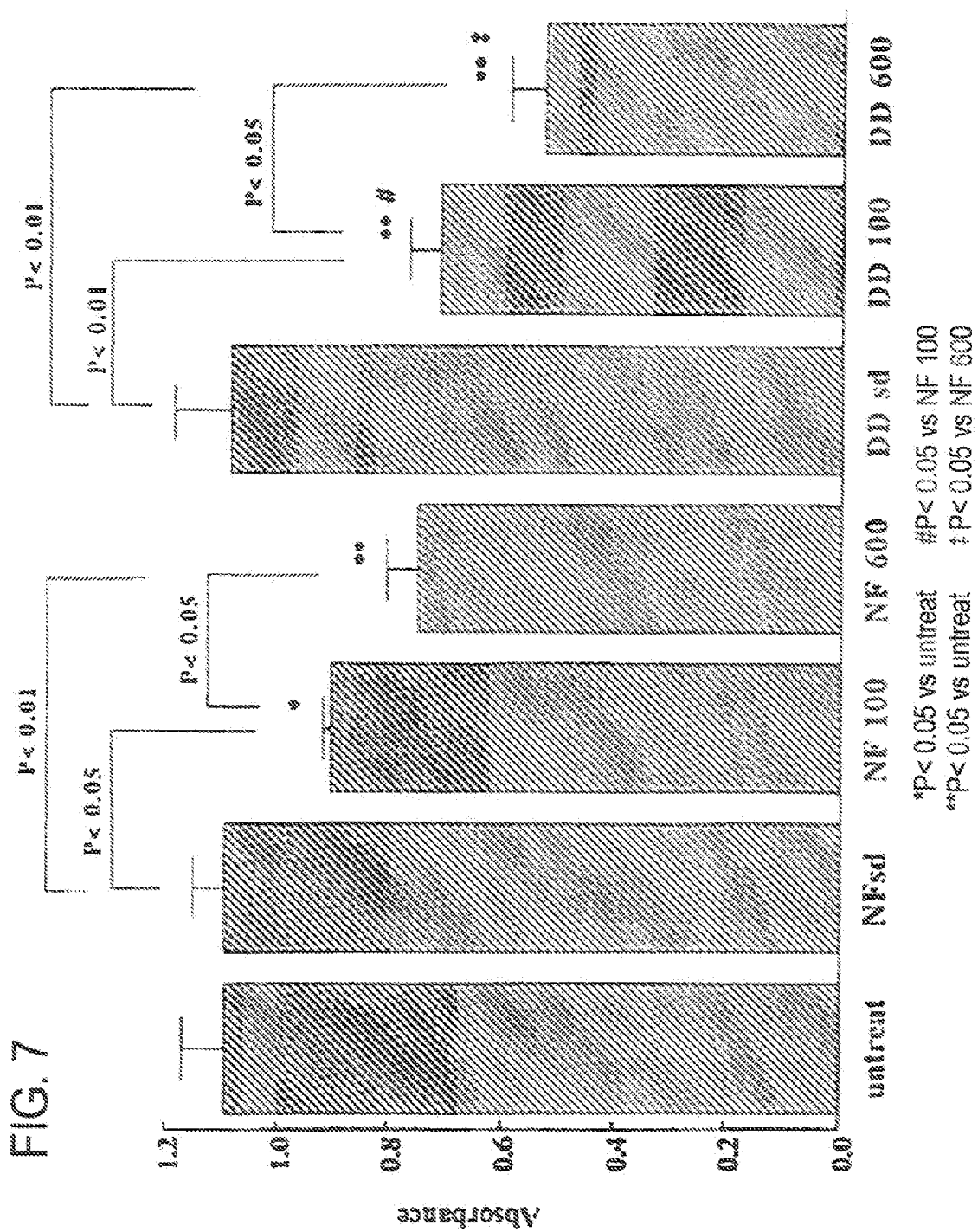
FIG. 7 shows the result of a test using the pharmaceutical composition of the present invention.

The results are shown in FIGS. 6 and 7. In FIGS. 6 and 7, the vertical axis represents absorbance at 450 nm, while "untreat", "NFsd", "NF100", "NF600", "DD sd", "DD100", and "DD600" on the horizontal axis represent no nucleic acid reagent (control), 100 μM NF-κB decoy, 600 μM NF-κB decoy, double scrambled decoy, 100 μM double decoy, and 600 μM double decoy. In FIGS. 6 and 7, a horizontal bar on each bar represents a standard deviation, and "P" on a line connected between each bar represents the level of significance which is used to compare groups connected via the line. "*" and "**" indicate that there is a statistically significant difference in average value between the group and the control with a significance level of 5% and 1%, respectively. "#" and "‡" indicate that there is a significant difference in average value between the NF100 or NF600 group and the control with a significance level of 5% (Fisher test).

As can be seen from FIGS. 6 and 7, production of MMP1 and MMP9 in the NF-κB-administered group was significantly suppressed as compared to the control group and the NF-κB scrambled decoy-administered group, and this effect was concentration-dependent. Also, production of MMP1 and MMP9 in the double decoy-administered group was suppressed as compared to the scrambled decoy-administered group. The effect of the double decoy was more significant as compared to the NF-κB decoy-administered group.

Example 4

In Vivo Effect of Decoy Nucleic Acid

Rats were used to test an effect of decoy nucleic acid in vivo administration on suppression of MMP gene expression.

Rats (SD rats, 12 weeks old) were anesthetized and abdominal incisions were performed. The abdominal aorta was wrapped over a length of about 1 cm with AD film (dimensions: 1 cm×1 cm) described below. The abdominal incisions were closed and the animals were kept in normal situations. After 3 day, the abdominal incisions were performed again to remove blood vessels, followed by fluorescent microscopic analysis.

The composition of the AD film is: hydroxypropyl cellulose 150 to 400 cps (HPC-M) 73 mg/4 cm$^2$; polyethylene glycol 400 (PEG) 7.3 mg/4 cm$^2$; FITC-labeled decoy 100 nmol/cm$^2$.

Method for preparing the AD film is: initially, the above-described hydroxypropyl cellulose and polyethylene glycol were dissolved in 100% ethanol and mixed together. 400 nmol of the FITC-labeled decoy was added and dissolved in the mixture, followed by air drying, to finally form a sheet of 4 cm$^2$.

Figure 8:
FIG. 8 shows fluorescent micrographs of cross sections of the rat abdominal aorta wall indicating the result of a test using the pharmaceutical composition of the present invention.
Figure 9:
FIG. 9 shows fluorescent micrographs of cross sections of the rat abdominal aorta wall indicating the result of a test using the pharmaceutical composition of the present invention.

The results are shown in FIGS. 8 and 9. FIG. 8 shows fluorescent micrographs (×200) showing partial cross sections of the abdominal aorta walls. A photograph to the left of FIG. 8 is a fluorescent micrograph showing a cross section of the abdominal aorta wall of the control rat, which was wrapped with the AD film not containing the FITC-labeled decoy. A photograph to the right of FIG. 8 is a fluorescent micrograph showing a cross section of the abdominal aorta wall of the control rat, which was wrapped with the AD film containing the FITC-labeled decoy. FIG. 9 shows fluorescent micrographs showing a cross section and a partial cross section of the abdominal aorta wall. A photograph to the left of FIG. 9 is a 100-fold magnification fluorescent micrograph. A photograph to the right of FIG. 9 is a 200-fold magnification fluorescent micrograph.

As can be seen from FIGS. 8 and 9, strong green color fluorescence is observed in the vascular adventitia of the abdominal aorta wall of the rat wrapped with the AD film containing the FITC-labeled decoy, and green fluorescence is observed in the media thereof. Thus, it was confirmed that the decoy was introduced into the vascular adventitia and a part of the vascular media.

Example 5

Effect of Decoy Nucleic Acid on Aortic Aneurysm Model Rats

Aortic aneurysm model rats have been established (Holmes D. R., Petrinec D., Wester W., Thompson R. W., Reilly J. M., "Indomethacin prevents elastase-induced abdominal aortic aneurysms in the rat", J. Surg. Res., 1996, June; 63 (1):305-9). This model can be produced by retaining elastase in the rat aorta under a pressure of 150 cm $H_2O$ for 30 min.

As shown in FIG. 10, the cross section area of the aorta was significantly increased in the aortic aneurysm model rats which received the scrambled decoy. In contrast, such an increase was significantly suppressed after two weeks ("2 W" on the horizontal axis in FIG. 10) and after three weeks ("3 W") in the NF-κB and ets double decoy-administered group.

INDUSTRIAL APPLICABILITY

The present invention provides a pharmaceutical composition for treating diseases caused by expression of a gene controlled by NF-κB or ets. The present invention also provides a carrier used for the composition. The topical administration of the pharmaceutical composition is non-invasive. Therefore, the present invention provides a repeatable therapeutic method.

The invention claimed is:

1. A method for treating a disease selected from the group consisting of aneurysm, Marfan's syndrome, and aortic detachment in a subject in need thereof;
   wherein said method comprises administering a composition comprising an NF-κB oligonucleotide decoy; and a pharmaceutically acceptable carrier to the subject.

2. The method of claim 1, wherein the aneurysm is abdominal aneurysm.

3. The method of claim 1, wherein the NF-κB oligonucleotide decoy comprises the nucleic acid sequence of SEQ ID NO: 1.

4. The method of claim 2, wherein the NF-κB oligonucleotide decoy comprises the nucleic acid sequence of SEQ ID NO: 1.

5. The method of any one of claims 1 and 2-4, wherein the acceptable carrier is a hydrophilic polymer.

6. The method of any one of claims 1 and 2-4, comprising contacting a target blood vessel in the subject with said composition, wherein the composition is shaped into a sheet, and the pharmaceutically acceptable carrier is a hydrophilic polymer.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: NF-?B decoy
<300> PUBLICATION INFORMATION:

<400> SEQUENCE: 1
ccttgaaggg atttccctcc                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: NF-?B
      scramble decoy
```

```
<400> SEQUENCE: 2
ttgccgtacc tgacttagcc                                                      20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: ets decoy

<400> SEQUENCE: 3
aattcaccgg aagtattcga                                                      20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: ets
      scramble decoy

<400> SEQUENCE: 4
ggaatacatc gacctgttaa                                                      20

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: double
      decoy

<400> SEQUENCE: 5
accggaagta gaagggattt ccctcc                                               26

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: double
      sramble decoy

<400> SEQUENCE: 6
gcaacccctt aggttctgag agacga                                               26
```